(12) United States Patent
Wolleschensky (10) Patent No.: US 7,170,696 B2
(45) Date of Patent: Jan. 30, 2007

(54) METHOD AND ARRANGEMENT FOR DEEPLY RESOLVED OPTICAL DETECTION OF A SAMPLE

(75) Inventor: Ralf Wolleschensky, Schoeten (DE)

(73) Assignee: Carl Zeiss Jena GmbH, Jena (DE)

( * ) Notice: Subject to any disclaimer, the term of this patent is extended or adjusted under 35 U.S.C. 154(b) by 407 days.

(21) Appl. No.: 10/425,302

(22) Filed: Apr. 29, 2003

(65) Prior Publication Data

US 2004/0095576 A1 May 20, 2004

(30) Foreign Application Priority Data

Nov. 15, 2002 (DE) ................................ 102 54 139

(51) Int. Cl.
*G02B 5/04* (2006.01)
*G02B 27/12* (2006.01)
*G01N 21/64* (2006.01)

(52) U.S. Cl. ........................ 359/831; 359/640; 359/837
(58) Field of Classification Search ................ 359/831, 359/837, 640
See application file for complete search history.

(56) References Cited

U.S. PATENT DOCUMENTS

| 4,826,299 A | 5/1989 | Powell |
| 5,192,980 A | 3/1993 | Dixon et al. |

FOREIGN PATENT DOCUMENTS

| DE | 195 10 102 | 10/1996 |
| DE | 199 02 625 | 9/1999 |
| DE | 100 17 825 | 10/2001 |
| EP | 1 008 845 | 6/2000 |
| EP | 101 20 425 | 10/2002 |
| WO | WO 95/07447 | 3/1995 |
| WO | WO 97/06509 | 2/1997 |
| WO | WO 02/12864 | 2/2002 |

OTHER PUBLICATIONS

Pawley, "Handbook of Biological Confocal Microscopy", Plenum Press 1995.
Corle, Kino, "Confocal Scanning, Optical Microscopy and Related Imaging Systems", Academic Press 1996.
T. Wilson, et al., "Method of obtaining optical sectioning by using structured light in a conventional microscope", Optics Letters 22 (24), 1997.
"Flow Cytometry and Sorting", 2nd edition, M. R. Melamed, T. Lindmo, M. L. Mendelsohn, eds., Wiley & Sons, Inc., New York, 1990, 81-107.
"Diffractive optics improve product design", Photonics Spectra, Laurin Publishing Co., Inc., Sep. 1995.

*Primary Examiner*—F. L. Evans
(74) *Attorney, Agent, or Firm*—Reed Smith LLP (57) ABSTRACT

A method and arrangement for the depth-resolved optical detection of a specimen with an illumination light distribution of at least one wavelength generated on or in a specimen and detection particularly of the light that is influenced due to interaction with the specimen, particularly fluorescent light and/or reflected light and/or luminescent light and/or scattered and/or transmitted light, wherein the illumination light has a modulation in at least one spatial direction and the detection light which is modulated like the illumination light is spatially split into two components having a phase shift relative to one another, the components are measured separately and an optical section image of the specimen and/or of part of the specimen is calculated from them.

6 Claims, 8 Drawing Sheets

METHOD AND ARRANGEMENT FOR DEEPLY RESOLVED OPTICAL DETECTION OF A SAMPLE

CROSS-REFERENCE TO RELATED APPLICATION

This application claims priority of German Application No. 102 54 139, filed Nov. 15, 2002, the complete disclosure of which is hereby incorporated by reference.

BACKGROUND OF THE INVENTION a) Field of the Invention

The invention is directed to a method and an arrangement in microscopy, particularly fluorescence microscopy, for examining predominantly biological specimens, preparations and associated components. This includes methods for screening active ingredients (high throughput screening) based on fluorescence detection. Simultaneous examinations of fluorescence specimens in real time by means of simultaneous illumination of the specimen in a plurality of points on the specimen are possible.

b) Description of the Related Art

A typical area of application of light microscopy for examining biological preparations is fluorescence microscopy (Pawley, "Handbook of Biological Confocal Microscopy", Plenum Press 1995). In this case, determined dyes are used for specific labeling of cell parts.

The irradiated photons having a determined energy excite the dye molecules from the ground state to an excited state by the absorption of a photon. This excitation is usually referred to as single-photon absorption. The dye molecules excited in this way can return to the ground state in various ways. In fluorescence microscopy, the transition with emission of a fluorescence photon is most important. Because of the Stokes shift, there is generally a red shift in the wavelength of the emitted photon in comparison to the excitation radiation; that is, it has a greater wavelength. Stokes shift makes it possible to separate the fluorescence radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, several parts of a preparation can also be dyed simultaneously with different dyes which bind in a specific manner (multiple fluorescence).

Special dichroic beam splitters are used again to distinguish between the fluorescence signals emitted by the individual dyes.

In addition to excitation of dye molecules with a high-energy photon (single-photon absorption), excitation with a plurality of low-energy photons is also possible. The sum of energies of the single photons corresponds approximately to a multiple of the high-energy photon. This type of excitation of dyes is known as multiphoton absorption (Corle, Kino, "Confocal Scanning, Optical Microscopy and Related Imaging Systems", Academic Press 1996). However, the dye emission is not influenced by this type of excitation, i.e., the emission spectrum undergoes a negative Stokes shift in multiphoton absorption; that is, it has a smaller wavelength compared to the excitation radiation. The separation of the excitation radiation from the emission radiation is carried out in the same way as in single-photon excitation.

In a method according to the prior art, known as structured illumination, the modulation depth of the optical imaging of an amplitude structure (e.g., grating) is used as a criterion for the depth of field. The image of the periodic structure is distinguished by the frequency of the modulation and the phase position (image phase) of the modulation. Various projection scenarios can be obtained by means of a phase shift of the structure at right angles to the optical axis. Generally, at least three phase images PB are required at 0°, 120° and 240° to calculate depth-discriminated optical sections without stripes. These phase images (PB) are subsequently calculated to form a (confocal) optical section image in an image processor by the following formula:

$$I_{Section}(x) = Const \cdot \sqrt{(I(x,0°)-I(x,120°))^2 + (I(x,120°)-I(x,240°))^2 + (I(x,0°)-I(x,240°))^2},$$

where I(x, angle) describes the intensity at the respective pixel in the corresponding phase image.

Figure 1:
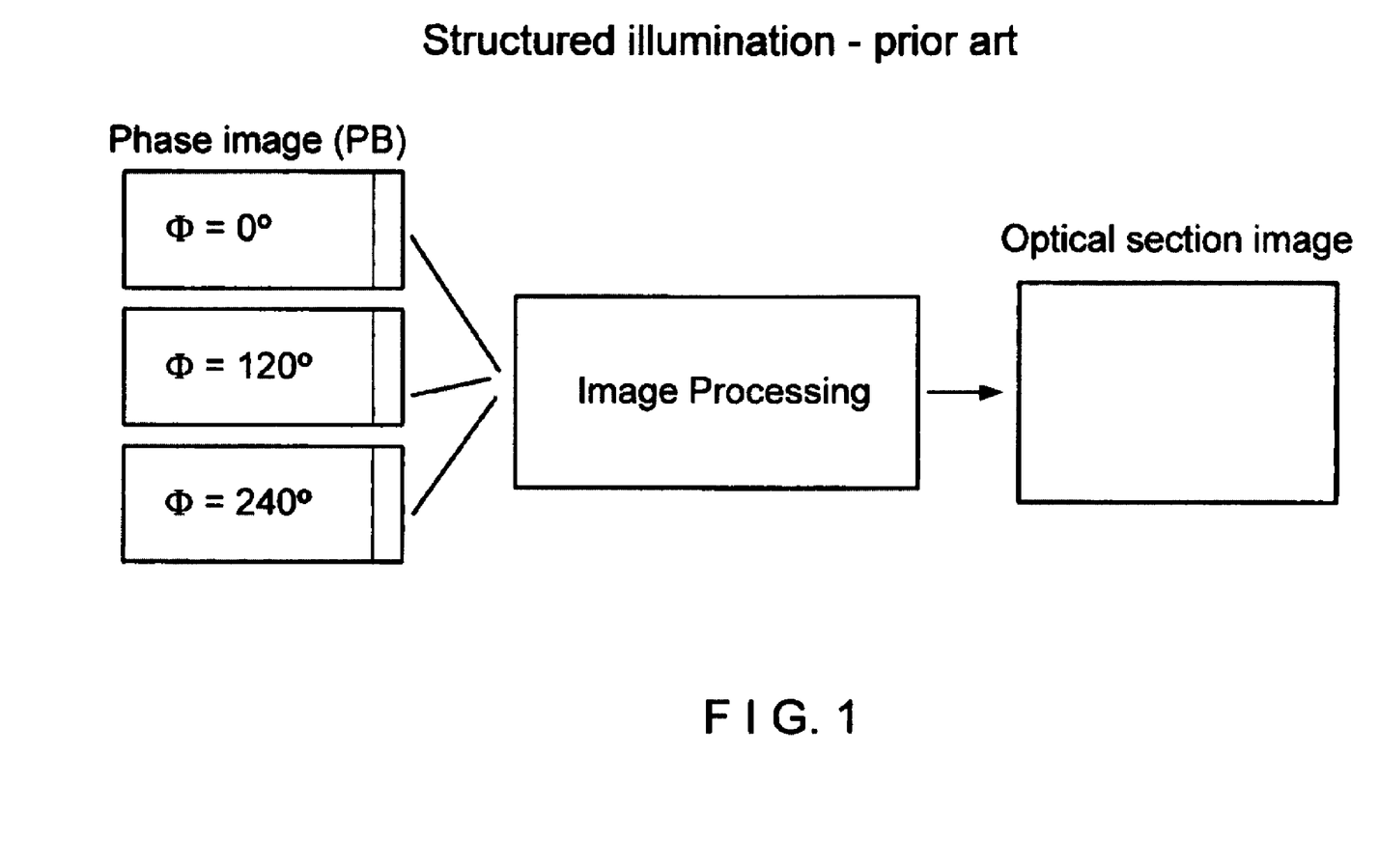
FIG. 1 illustrates in block diagram form, structured illumination according to the prior art.

The measuring sequence for generating an optical section image is shown schematically in FIG. 1. It is simplest to carry out the recording of three or more phase images sequentially. In this connection, it is assumed that the specimen is not moved during the measurement of the images. The section images or section stacks which are calculated in this way from the phase images can be displayed subsequently on a standard PC and monitor by means of 3-D evaluating software.

The spatial resolution along the optical axis depends on the wavelength of the light, the numerical aperture of the objective and the modulation frequency.

For a detailed description of the calculation algorithm, reference is had to T. Wilson, et al., "Method of obtaining optical sectioning by using structured light in a conventional microscope", Optics Letters 22 (24), 1997, and WO9706509.

From a three-dimensionally illuminated image, only the plane (optical section) located in the focal plane of the objective is reproduced in connection with the corresponding single-photon absorption or multiphoton absorption. By recording a plurality of optical sections in the x-y plane at different depths z of the specimen, a three-dimensional image of the specimen can be generated subsequently in computer-assisted manner.

Therefore, structured illumination is suitable for examination of thick preparations. The excitation wavelengths are determined by the utilized dye with its specific absorption characteristics. Dichroic filters adapted to the emission characteristics of the dye ensure that only the fluorescent light emitted by the respective dye will be measured by the point detector.

Figure 2A:
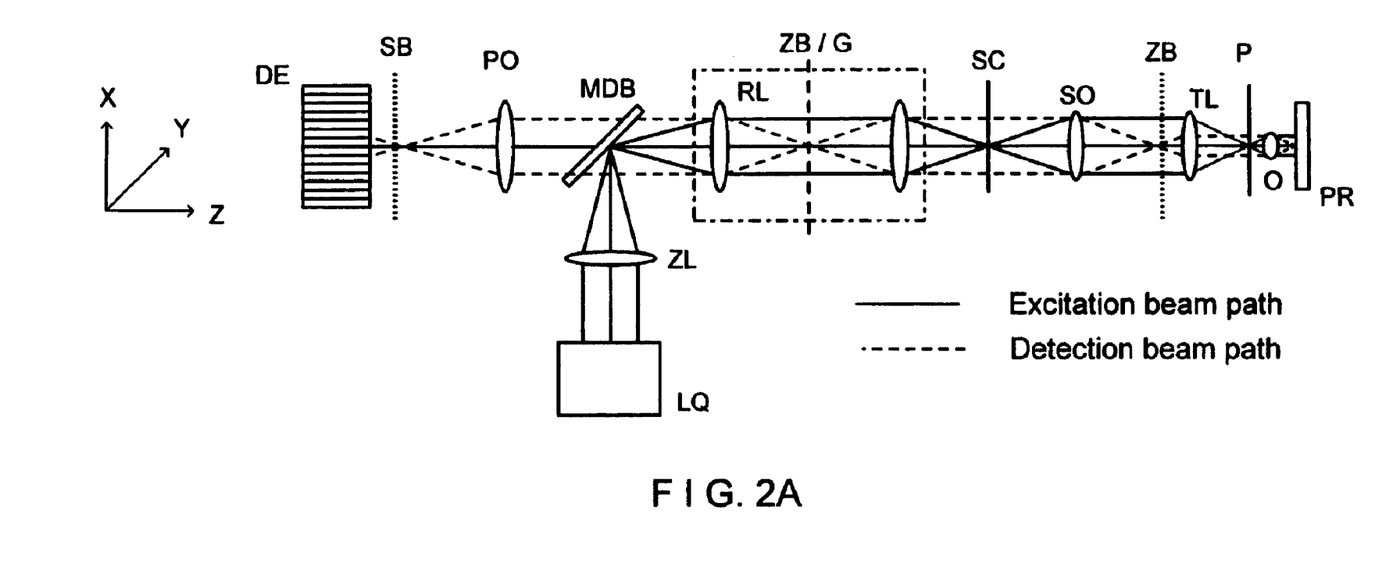
FIG. 2A illustrates the top view, in schematic form, of a line scanner in accordance with the invention.

Flow cytometers are used for examining and classifying cells and other particles. For this purpose, the cells are dissolved in a liquid and are pumped through a capillary. In order to examine the cells, a laser beam is focused in the capillary from the side. The cells are dyed with different dyes or fluorescing biomolecules. The excited fluorescent light and the backscattered excitation light are measured. The separation of the fluorescence signal of the specimen from the excitation light is carried out by means of dichroic beam splitters (MDB, see FIG. 2). The art is described in "Flow Cytometry and Sorting", 2nd edition, M. R. Melamed, T. Lindmo, M. L. Mendelsohn, eds., Wiley & Sons, Inc., New York, 1990, 81–107.

The size of the cells can be determined from the backscattered signal. Different cells can be separated and/or sorted or counted separately by means of the spectral characteristics of the fluorescence of individual cells. The sorting of the cells is carried out with an electrostatic field in different capillaries. The results, that is, for example, the quantity of cells with dye A in comparison to cells with dye B, are often displayed in histograms.

The through-flow rate is typically about 10–100 cm/s. Therefore, a highly sensitive detection is necessary. According to the prior art, a confocal detection is carried out in order to limit the detection volume.

Arrangements for screening dyes, for example, in so-called chip readers are similar in optical construction to a laser scanning microscope. However, they scan an appreciably larger image field for the examination of macroscopic specimens, for example, screening of active ingredients on a biochip. The edge length of the scan fields amounts to about 10 mm. These scan fields can be achieved, e.g., by increasing the scan angle of the galvoscanner, by arranging the specimen in an intermediate image of the microscope arrangement, for example, in FIG. 7A, or by a special objective arrangement (macroobjective) which images the intermediate image on the specimen in magnified manner.

A disadvantage in the prior art consists in that a plurality of images must be sequentially recorded, read out and calculated. In particular, this imposes increased requirements on the adjusting unit for the different projection scenarios, because otherwise residual modulations (residual structures) would remain in the image. In addition, the speed at which confocal section images can be generated is reduced by a factor of 3 when recording three phase images. Further, the usable dynamic range of the detector is limited depending on the strength of the nonconfocal background signal of the specimen (i.e., signals outside of the focal plane).

OBJECT AND SUMMARY OF THE INVENTION

The primary object of the invention is to provide a method and apparatus which overcomes the problems and disadvantages of the prior art.

In accordance with the invention, a method for the depth resolved optical detection of a specimen with an illumination light distribution of at least one wavelength generated on or in a specimen and detection particularly of the light that is influenced due to interaction with the specimen, particularly fluorescent light and/or reflected light and/or luminescent light and/or scattered and/or transmitted light, comprising the steps of providing illumination light having a modulation in at least one spatial direction, spatially splitting detection light, which is modulated like the illumination light, into two components having a phase shift relative to one another and measuring at least one in-phase component or out-of-phase component for recording an optical section image.

An arrangement and a prismatic element in accordance with the invention are also described and claimed herein.

By means of the arrangements according to the invention, it is possible to generate the optical section images already at the detector. This prevents limiting of the dynamic range of the detector due to nonconfocal background signals. A sequential recording and readout of the phase images for calculating in the PC is no longer necessary, so that the speed of the detector is entirely available for the recording of confocal section images. Residual modulations in the confocal section image are prevented.

The solution according to the invention is usable in image-generating as well as analytic microscope systems.

BRIEF DESCRIPTION OF THE DRAWINGS

In the drawings:

FIGS. 4 and 4A show in schematic form an arrangement of the grating in the ZB/G by way of example;

DESCRIPTION OF THE PREFERRED EMBODIMENTS

Figure 2B:
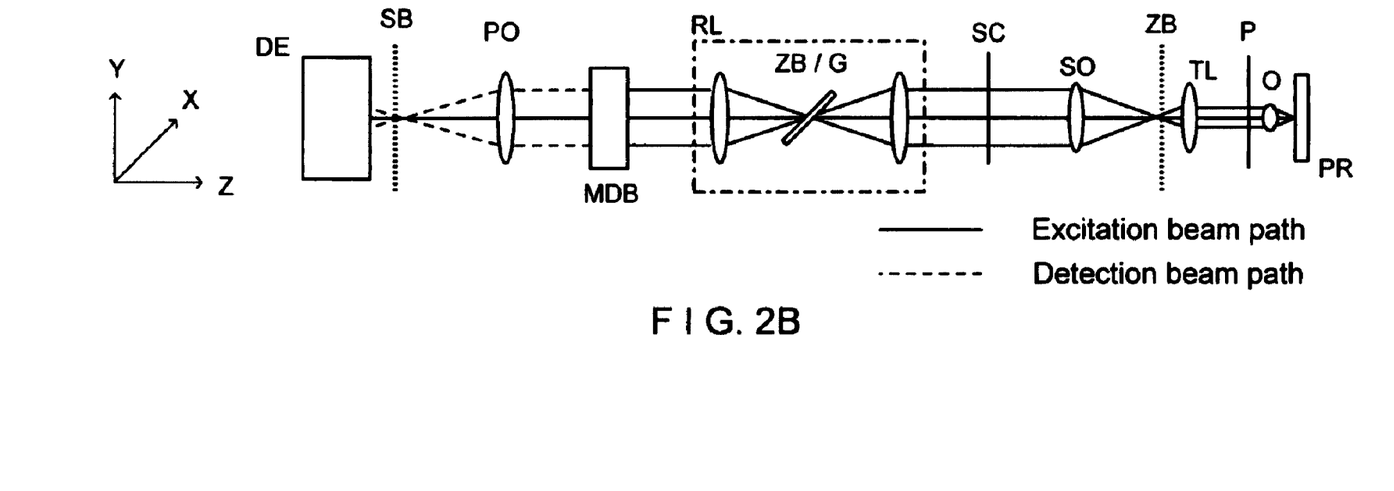
FIG. 2B illustrates the side view, in schematic form, of a line scanner in accordance with the invention.

The arrangement, according to the invention, for a line scanner is shown schematically in FIG. 2A (side view) and FIG. 2B (top view). The solid lines in the beam path represent the illumination beam path. The dashed lines represent the detection beam path. In a line scanner, the specimen is illuminated by a line focus, e.g., along the X coordinate which is shifted in the coordinate vertical to the line. For this purpose, the light source LQ (FIG. 2A), which can radiate one wavelength or a plurality of wavelengths as well as wavelength bands or which can be a white light source, is focused in a line-shaped manner in an intermediate image plane ZB of the microscope device by means of optics ZL, cylindrical lens, and optics RL, relay lens. A diffraction-limited, line-shaped intensity distribution results along the X coordinate on the specimen PR by focusing in Y-direction in the second intermediate image ZB/G, where G is an amplitude grating, after traversing the scanner SC, scanning optics SO, a tube lens TL and an objective O. P is a pupil of the microscope arrangement. Further, the line-shaped intensity distribution along X on the specimen can be carried out by diffractive or holographic elements according to the prior art ("Diffractive optics improve product design", Photonics Spectra, Laurin Publishing Co., Inc., September 1995). For this purpose, the diffractive element is arranged in a pupil of the microscope, preferably in the excitation beam path. Further, a Powell lens, as it is called, such as is described in U.S. Pat. No. 4,826,299, can be used. The latter element generates a more homogeneous intensity distribution along the line compared to the cylindrical lens with Gaussian illumination intensity distribution as is typical, e.g., for single-mode lasers. For this purpose, the Powell lens and the diffractive or holographic elements are arranged in a particularly advantageous manner, for example, in a pupil plane of the microscope device, between the light source and scanner. The light is imaged in the pupil SC of the microscope arrangement by relay optics RL. A line focus results along the Y-axis in the pupil planes P, SC and MDB of the microscope arrangement. The pupil planes SC and the plane in which the main color splitter MDB is located are pupil planes of the microscope arrangement that are conjugate to one another and to the back focal plane of the objective (P), so that the line-shaped intensity distribution which is focused in a diffraction-limited manner can be moved by the scanner vertical to the line focus in the specimen (y-coordinate in the specimen). The imaging of ZB to the specimen is carried out via the scanning optics (SO), the tube lens (TL) and the objective (O). The relay optics (RL) generate the conjugate pupil planes MDB and SC of the microscope arrangement. In special arrangements according to the prior art, the relay optics can also be dispensed with. For example, they can be omitted when the distance between MDB and SC is reduced. Further, the element MDB arranged on a scanner can also be used directly in SC for scanning the line focus in Y-direction. In this arrangement, the relay optics and accordingly the pupil plane MDB can be entirely omitted. In principle, the transmissive optics ZL for shaping the line can also be replaced by a reflecting element, e.g., a cylindrical mirror, whose focal point lies on MDB. The cylindrical mirror is then arranged (not shown) at 45° in the xz-plane shown in FIG. 7A. The mirror also has its focusing effect in this plane. Further, the beam path is angled at 90° to the light source by the mirror.

The observation beam path in reverse direction to a detector DE (spatially resolving), e.g., in fluorescence excitation, is shown in dashed lines. Based on the type of specimen interaction, e.g., with fluorescence excitation or luminescence excitation, the light emitted by the specimen has a low spatial coherence. This means that each point excited in the specimen radiates as a point radiator in all spatial directions so as to be essentially independent from the adjacent points. The optics O(e.g., a microscope objective) image the individual point radiators together with the tube lens TL in an intermediate image plane ZB of the microscope device, wherein the pupil P is uniformly illuminated by wavefronts of different propagation directions which are substantially incoherent relative to one another. Subsequently, the light of the specimen is focused by means of imaging optics (PO) with confocal detection through a slit diaphragm (SB) (slit position in longitudinal direction in X-direction in the drawing), so that detection light occurring outside of the focus is suppressed. A line detector or surface detector (DE) (position of line in X-direction) is located behind the slit diaphragm and detects the light radiation excited and/or backscattered in the specimen in a spatially resolved manner (along the line focus). The line focus is scanned in one spatial direction by the galvoscanner SC. When recording fluorescence or luminescence, an emission filter is swiveled into the detection beam path, preferably between PO and SB (dichroic filter) F for suppression of the excitation light backscattered from the specimen.

Components MDB and ZB/G will be described with reference to FIGS. 3 and 4.

Figure 3:
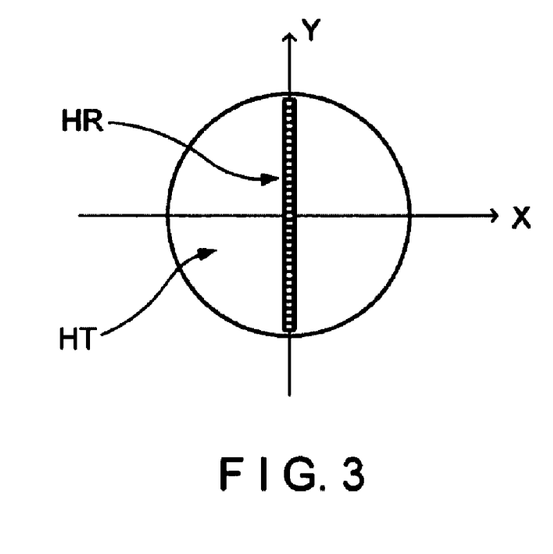
FIG. 3 shows an enlarged view of the element MDB in accordance with the invention.
Figure 4:
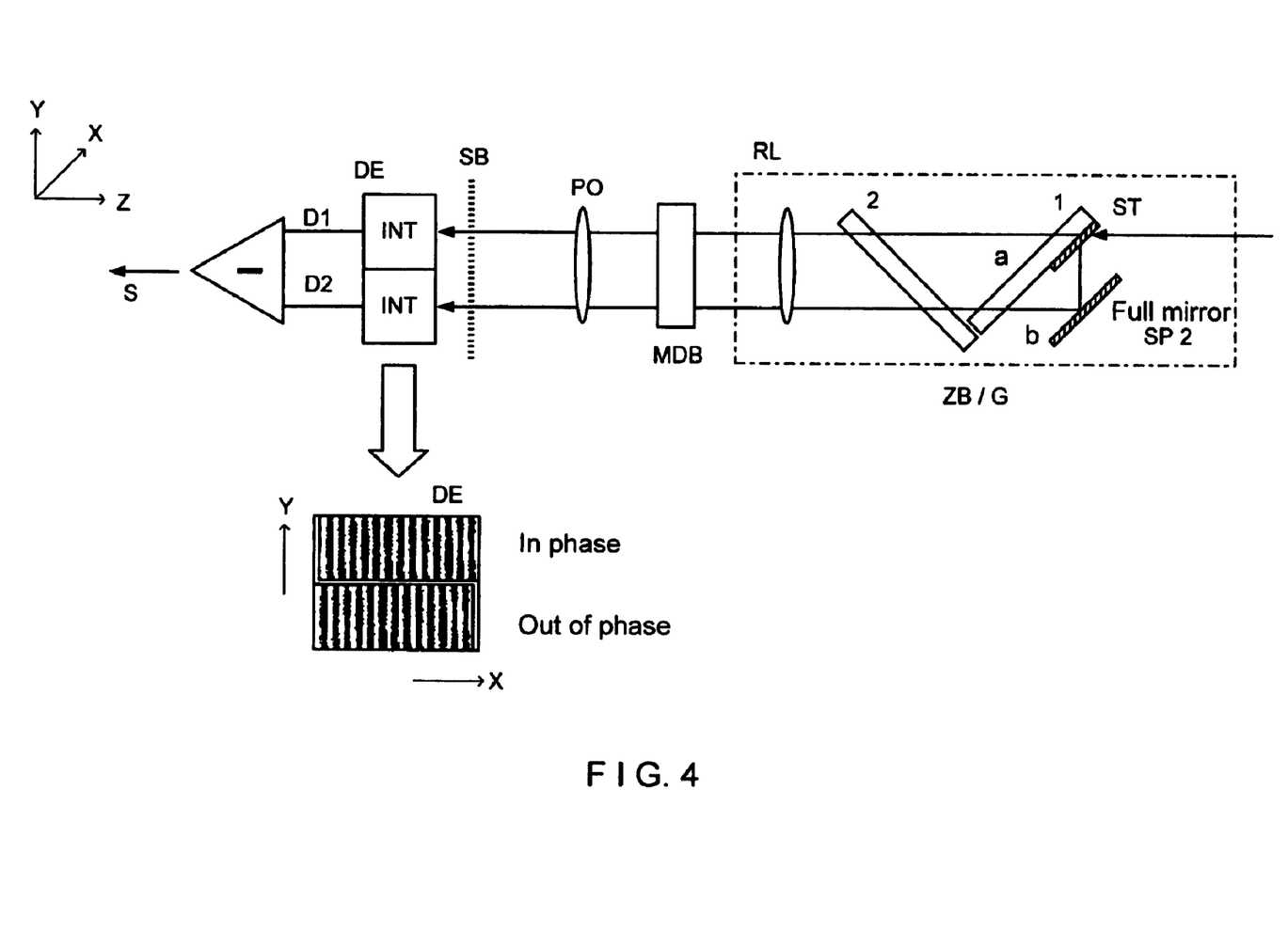

The element MDB shown in FIG. 3 which carries out the separation of the excitation light from the detection light is located in the pupil MDB. For purposes of illustration, the element MDB is shown in an enlarged view.

MDB is fully reflecting in the gray area HR. The white area HT is highly transmissive particularly for the wavelength range in which the specimen excitation is to be carried out. The outer border of the MDB shows the pupil diameter of the microscope unit. In the simplest case, the HR area can be a narrow mirror, which is sufficient for the input-reflection of the line. According to the invention, the excitation light is focused on the HR area. The light reflected on a direct path from the specimen arrives again at the light source particularly on the HR area. The excitation light diffusely scattered in the specimen and/or the light excited in the specimen strike(s) the entire surface of the MDB corresponding to the pupil size of the microscope optics; the proportion striking the HT area reaches the intermediate image SB/DE for observation. Only the portion of the detection radiation falling on the HR area is lost in this arrangement at MDB. The ratio of surfaces HT to HR is:

$$R = \frac{A_{Pupil} - A_{HT}}{A_{Pupil}} = \frac{\pi \cdot r_{Pupil} - b_{TH}}{\pi \cdot r_{Pupil}},$$

where the pupil radius for the HT area in a microscope is typically about 5 mm and the width of the HR area is approximately $b_{HT} < 0.25$ mm. Accordingly, the resulting ratio and, therefore, for the efficiency of the beam splitting of MDB independent from the wavelength, R=97%.

In FIG. 2B, a grating structure G is located at point ZB/G (intermediate image). The grating G, preferably a periodic rectangular grating or sine grating, has alternating areas of high transmission and high reflectivity. The grating lines are located along the Y axis, that is, transverse to the line generated through ZL. The grating is arranged in the yz-plane (FIG. 2B) so as to be tilted preferably by 45° to the X-axis and is preferably traversed by the excitation light and by the detection light. Other tilting angles enabling spatial splitting into partial beams a and b are also possible. Therefore, a structure is impressed on the excitation light along the scan line. FIG. 4a shows schematically an arrangement of the grating in the ZB/G by way of example. Detection light from the focus area travels in the direction indicated by the arrow to the grating with structure ST primarily to regions in which the grating is highly transmissive because this detection light is imaged sharply again at the location of structure ST on the return path in the direction of the detector. On the other hand, detection light from regions of the specimen which lie outside of the focus reach the regions with and without reflection coating in a uniformly distributed manner because it is not sharply imaged on the structure ST. Accordingly, the structure ST acts like a diaphragm or shutter for the detection light from the focus, so that signals from outside the focus are suppressed by at least 50%. The detection light which is modulated along the illumination line is split into two portions or components by the effect of the structure ST, the periodic structures of these two components having a phase shift of pi relative to one another. In the following, the two components are also referred to as in-phase component a and out-of-phase component b. Preferably, the out-of-phase component travels via a full mirror SP2 in the direction of the detector segment D2 and the in-phase component travels to detector segment D1. The in-phase component a carries the signal from the confocal section image A plus a background signal B multiplied (see formula below) by the in-phase component of structure ST. The out-of-phase component b carries the signal from the confocal section image A plus the background signal B multiplied (see formula below) by the out-of-phase component of structure ST. Both components are imaged on two detector lines DE through the pinhole optics PO. The image section in FIG. 4a shows the detector DE with the two lines. The in-phase and out-of-phase components of the imaged structure ST are shown schematically along the x-axis.

The measured quantities will be discussed in the following based on a cosine-shaped structure of the scan line with a period k along the x-axis because this simplifies the derivation of the analytic terms. It is a simple matter to transfer to different structures without restrictions. Assuming a cosine-shaped structure, the signal of the specimen F(x), the in-phase component D1(x) and the out-of-phase component D2(x) along the x-axis are as follows:

signal of the specimen: $F(x)=B(x)+A(x)\cdot(\cos(k\cdot x)+1)$ in-phase component: $D_1(x)=F(x)\cdot(\cos(k\cdot x)+1)$ out-of-phase component: $D_2(x)=F(x)\cdot(\sin(k\cdot x)+1)$ When considering a specimen point, this specimen point is illuminated with different brightness as the structure is displaced along the scan line. When the structure is displaced uniformly, e.g., also periodically, the cosine-shaped structure translates along the scan line into a cosine-shaped temporal modulation of the specimen signal, resulting in the following expression:

signal of the specimen: $F(x,\tau)=B(x)+A(x)\cdot(\cos(k\cdot\tau)+1)$ in-phase component: $D_1(x,\tau)=F(x)\cdot(\cos(k\cdot\tau)+1)$ out-of-phase component: $D_2(x,\tau)=F(x)\cdot(\sin(k\tau)+1)$ The detector DE integrates the in-phase component D1(x) and the out-of-phase component D2(x) over the pixel dwell time t and the integrated individual signals are then subtracted from one another, resulting in the following analytic expression for the integrated measurement signal S(x, t→infinity) based on a cosine-shaped structure:

Measurement Signal:

$$S(x, t) = \int_0^t D_1(x, \tau)\,d\tau - \int_0^t D_2(x, \tau)\,d\tau$$

$$S(x, t) = \frac{1}{t}\left([\sin(kt) + \cos(kt)] \cdot \left(B(x) + \frac{A(x)}{2}\cos(kt) + A(x)\right) + \frac{A(x)t}{2} - B(x) - \frac{3A(x)}{2}\right)$$

$$S(x, t \to \infty) = A(x)/2$$

The measurement signal S corresponds for large pixel dwell times t to the half signal from the optical section image, i.e., the desired information without background signal, which proceeds from planes outside the focus.

Figure 5:
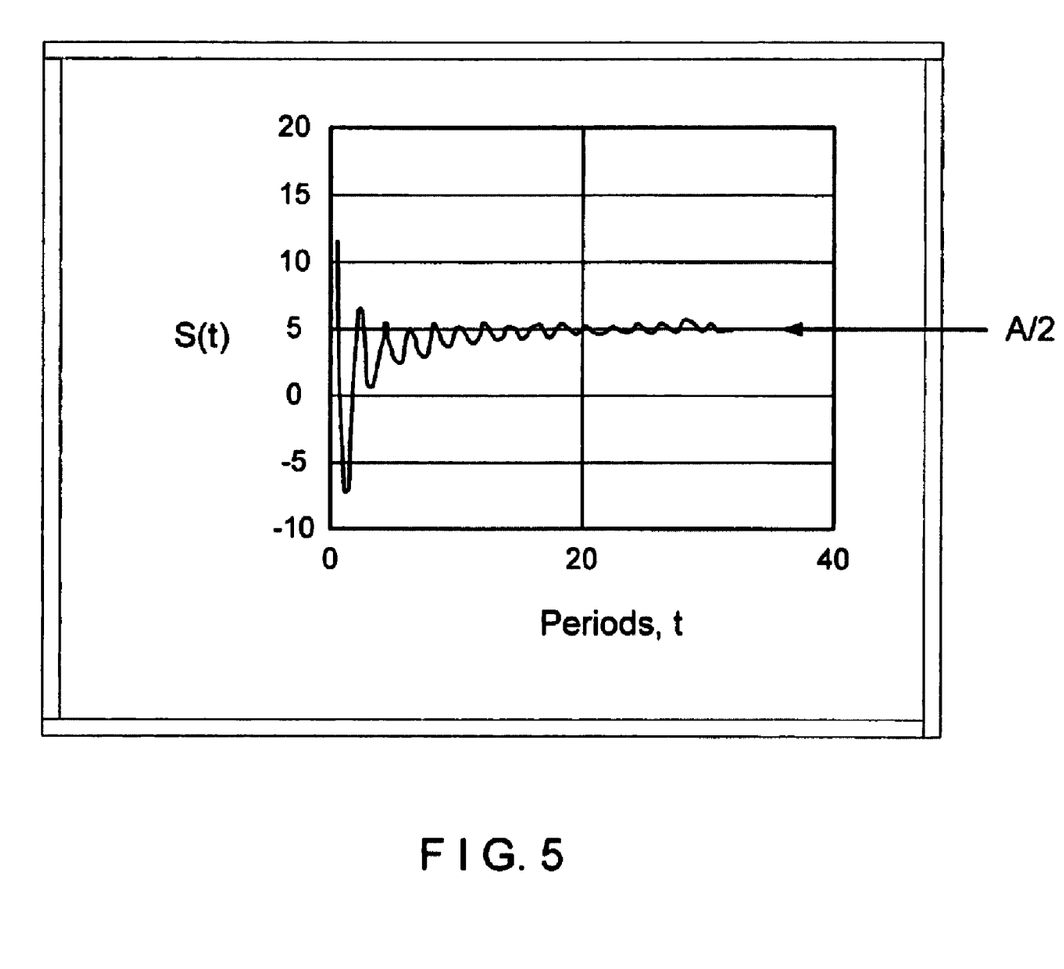
FIG. 5 shows the dependency of the measurement signal. S(t) on the pixel dwell time t for a constant location point x.

FIG. 5 shows the dependency of the measurement signal S(t) on the pixel dwell time t for a constant location point x. It will be seen that the measurement signal S for pixel dwell times t greater than 10 periods k already corresponds to the signal from the confocal section image A/2.

The displacement of the structure relative to the specimen can be carried out, for example, by means of a displacement of the grating G in x-direction or by means of a movement of the scanner SC in the coordinate generating a displacement along the x-coordinate on the specimen.

Figure 6:
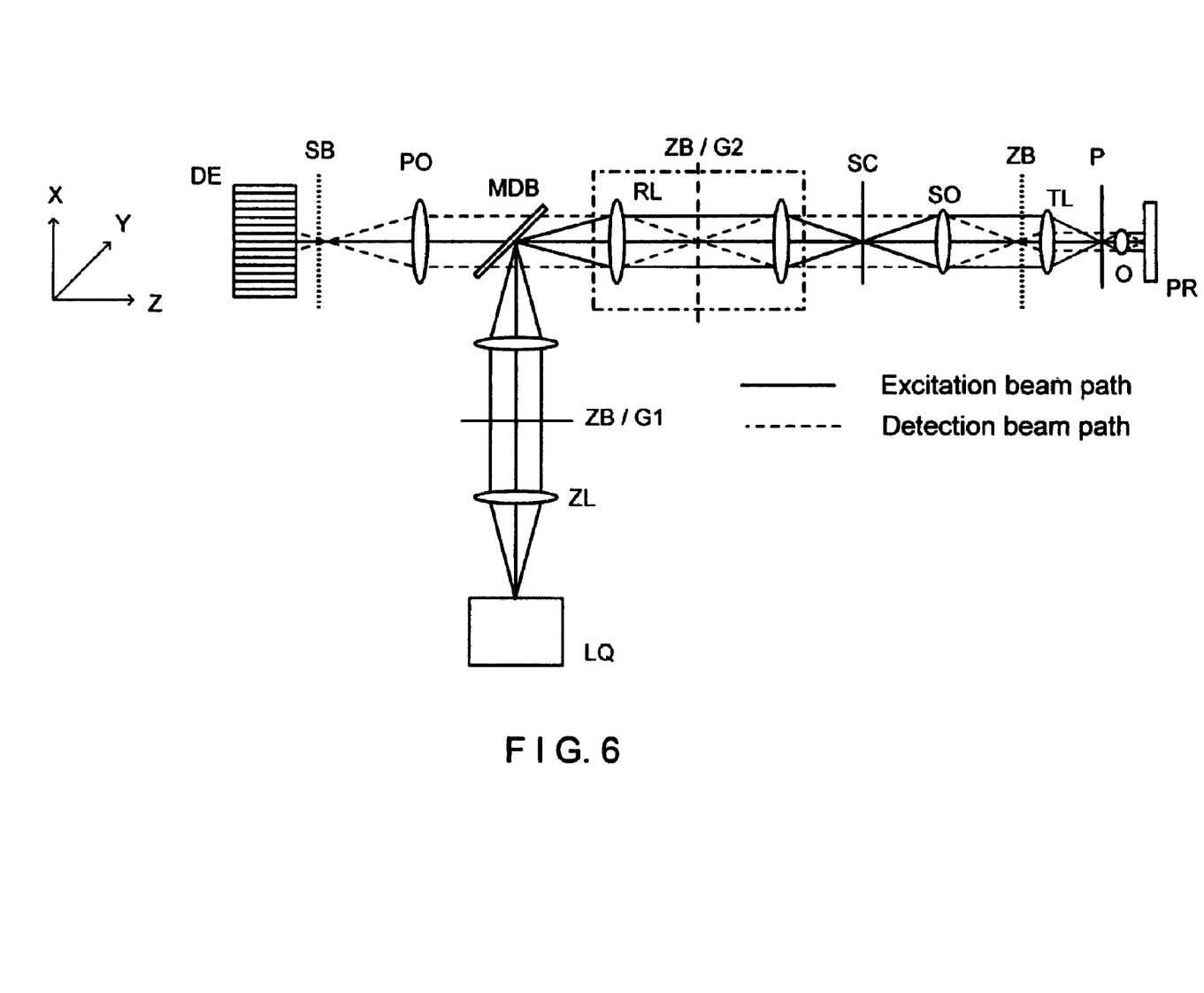
FIG. 6 graphically shows the effect of a phase or amplitude grating for increasing the transmission efficiency.

When using an amplitude grating, 50% of the energy of the excitation light is normally lost. In order to increase the transmission efficiency in the excitation beam path (see FIG. 6), , a phase grating or amplitude grating GI with the same grating frequency of an amplitude grating G2 which was already described in FIG. 4 can be inserted in front of the amplitude grating G2 and in the direction of the light source for generating an interference structure at point G2 in another intermediate image plane conjugate to the amplitude grating G2 in the excitation beam path which is generated by other relay optics (not shown). In this way, the energy of the excitation light is correspondingly redistributed in such a way that a more efficient imaging is carried out through the amplitude grating G2. Another advantage consists in that less scatter light from the excitation light at G2 which could travel in the direction of the detector is minimized. When illuminating the specimen via an interference structure advantageously, as is shown, between the light source and MDB, the grating element G2 can remain at its location or can also be placed in an intermediate image (SB) in front of the detector and can therefore act according to the invention for the light coming from the specimen.

Figure 7A:
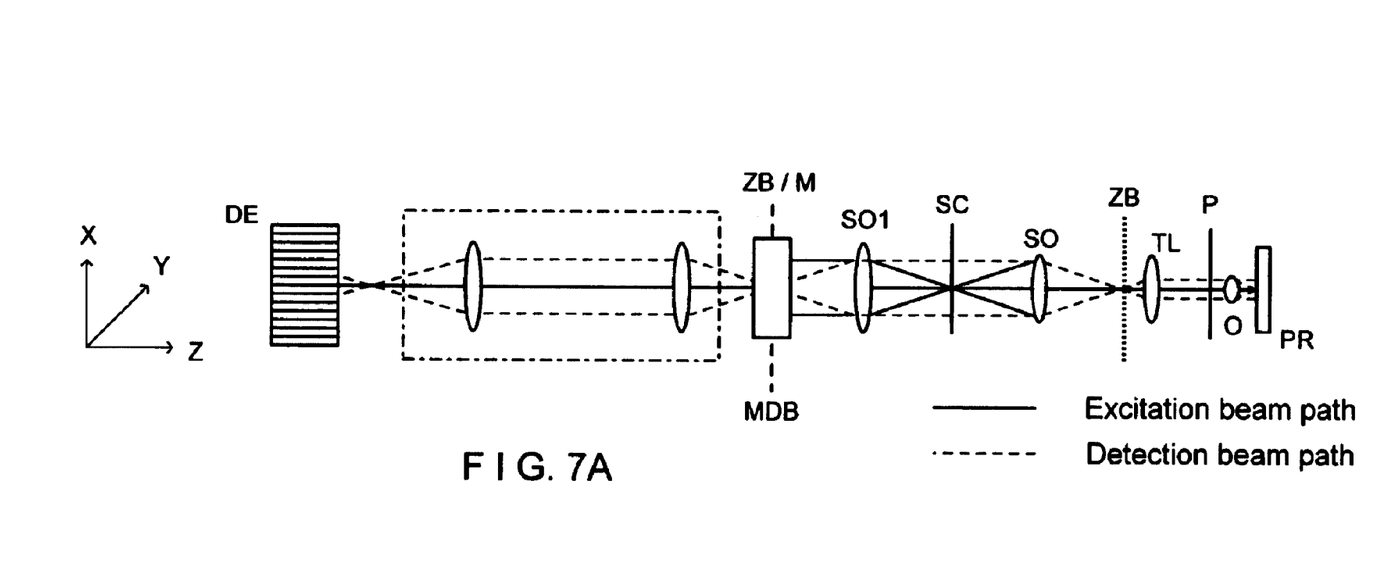
FIGS. 7A and 7B illustrate another arrangement, in schematic form, for dividing the excitation beam from the detection beam as a top view and side view, respectively.
Figure 7B:
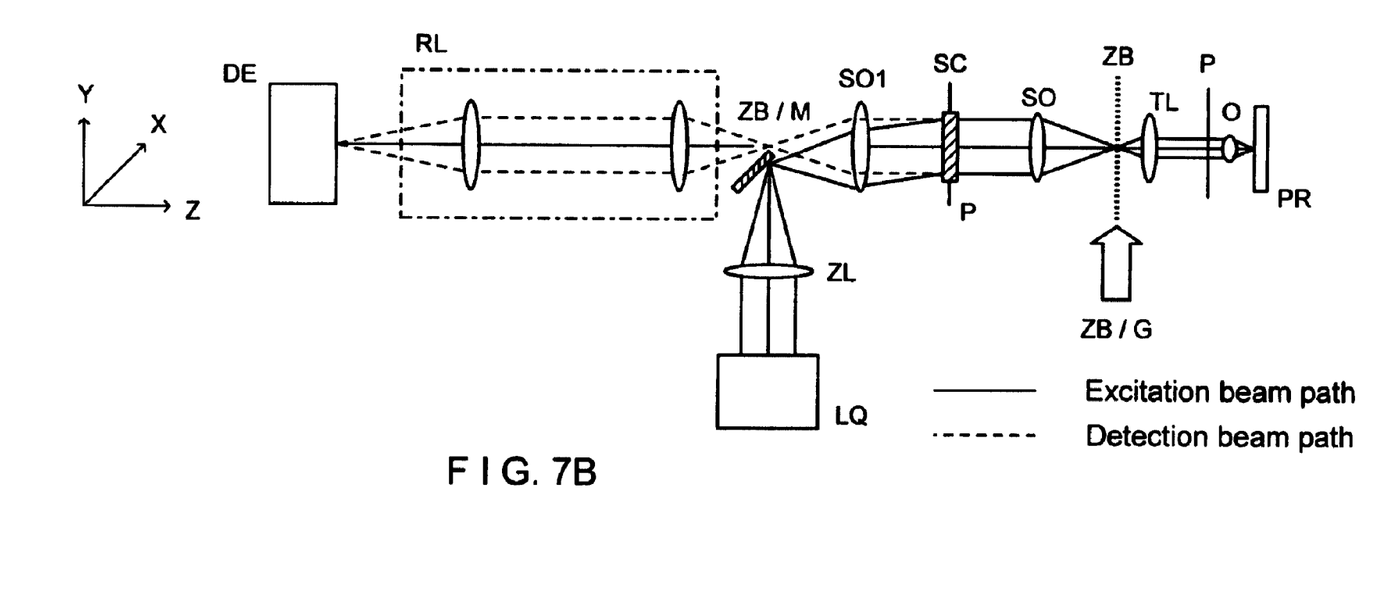

FIG. 7 shows another advantageous arrangement for dividing the excitation beam from the detection beam. The spatial separation is carried out in an intermediate image ZB/M; the detection beam or excitation beam is tilted by a prismatic element PR (the element is described in more detail in the following with reference to FIG. 8). The advantage of the arrangement consists in the use of the usually highly corrected optics RL for the excitation beam path and detection beam path.

The grating for the structure in an intermediate image plane ZB/G (see arrow) is shown in FIG. 7 between the tube lens TL and scanner SC. The shifting of the structure relative to the specimen can be carried out by displacing the structure or by using a wobble plate.

However, the grating G for the structure can also be arranged in an intermediate image plane between the scanners SC and the prismatic element P (not shown). This can be carried out, for example, through the use of additional relay optics for generating the additional intermediate image plane. This has the advantage that the scan line is not scanned via the grating, which can cause intensity fluctuations, e.g., due to irregularities on the grating. The shifting of the structure relative to the specimen can then also be carried out by means of a scanner SC.

The relay optics RL can also be dispensed with and the detector DE can be arranged directly in the plane ZB/M, so that the optical construction is even further simplified.

Figure 8A:
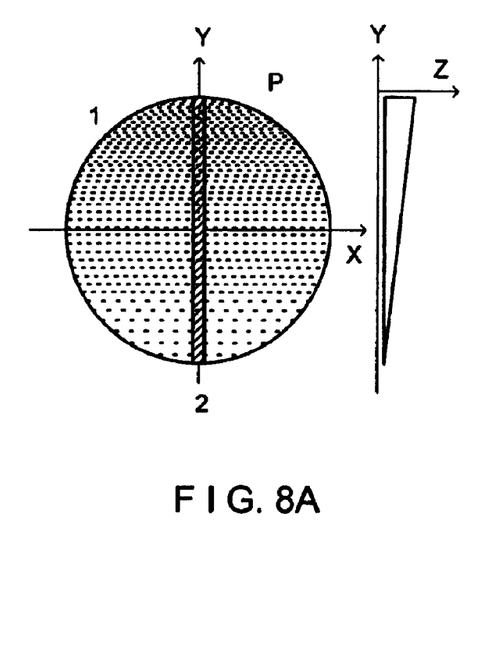
FIG. 8A shows a construction of the element P, by way of example, in an enlarged manner in the xy and yz plane.
Figure 8B:
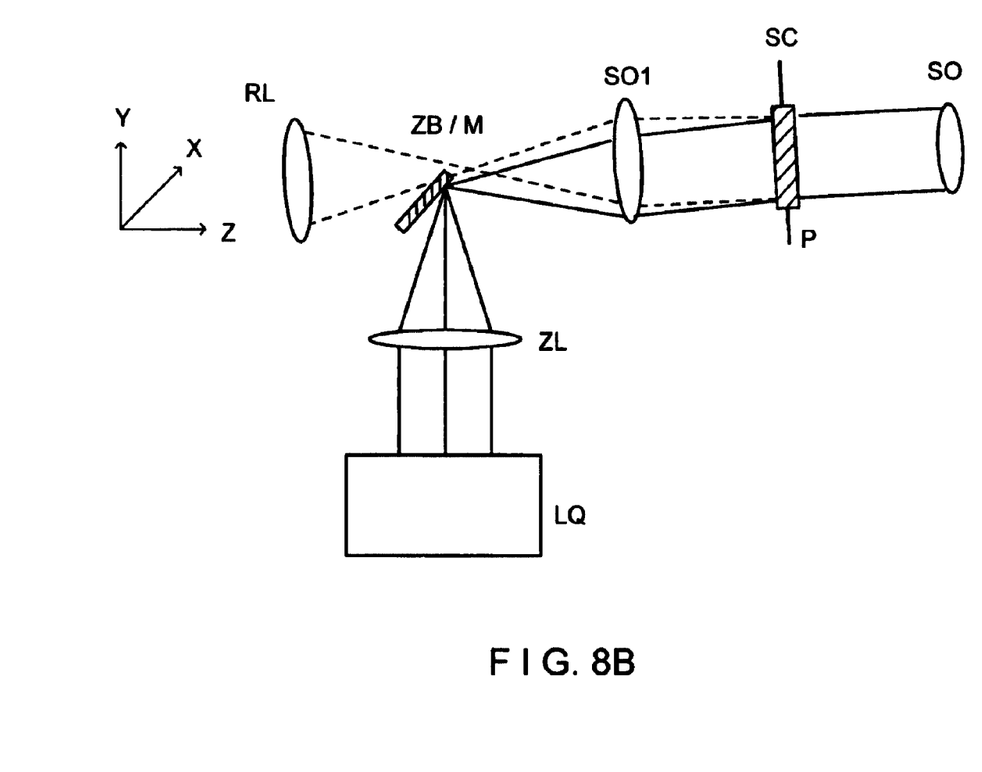
FIG. 8 shows the effect of the prismatic element in detail with the yz plane.

FIG. 8 shows the effect of the prismatic element in detail in the yz-plane. The drawing shows the elements comprising scanning optics SO, prismatic element PR/SC, scanning optics SO1, mirror M in plane ZB/M for mirroring out the excitation light. A construction of the element P is shown by way of example in FIG. 8A in enlarged manner in the xy-plane and yz-plane. The view on the right-hand side shows a section through the element PR in a region 1 outside of region 2.

The element is transmissive, wherein regions 1 (region shown in curve) are ground in the shape of a prism. Region 2 is plane-parallel (dark area). The beam striking region 2 (excitation beam) is accordingly deflected relative to the beam falling on region 1 (detection beam) vertical to the scan line (in the y-axis) and additionally divided into spectra. In the intermediate image, the variously deflected spectral components of the detection light (of region 1) and the excitation light (of region 2) reach different points, so that the excitation light and the detection light can be spatially separated. The spectral components that are spatially separated in the intermediate image ZB/M can be measured spectrally subsequently by a detector array which, for example, is arranged in the X-Y plane in FIG. 7. The detector elements along the Y coordinate measure the spectral information and the elements along the X-axis measure the information along the scan line, i.e., the spatially resolved information. In principle, regions 1 and 2 on the prismatic element PR can also be exchanged. A spectral splitting of the excitation beam can be carried out in this way, which can be compensated again by means known from the prior art or used to unify spectral components of the light source. Further, the transmissive element P can also be replaced by suitable mirror arrangements.

While the foregoing description and drawings represent the present invention, it will be obvious to those skilled in the art that various changes may be made therein without departing from the true spirit and scope of the present invention.

What is claimed is:

1. A prismatic element for use in a microscope adapted to perform depth-resolved optical detection of a specimen with an illumination light distribution of at least one wavelength generated on or in a specimen and detection light that is influenced due to interaction with the specimen, the prismatic element comprising:

at least one region which is plane-parallel; and a second prismatic region which carries out an angular deflection between the illumination light and detection light and which is arranged in a pupil plane of the microscope.

2. The prismatic element according to claim 1, wherein a spatial separation of the detection light from an excitation light is carried out in an intermediate image plane.

3. The prismatic element according to claim 1, wherein a spatial separation of the spectral components of the specimen signal is carried out by the prismatic surface of the element and these spectral components are measured by a detector array.

4. The prismatic element according to claim 1, wherein a spatial separation of the spectral components of an excitation light is carried out through the prismatic surface of the element and the spectral components are combined to form a common beam in the specimen.

5. The prismatic element according to claim 1, wherein the prismatic element has a plane-parallel plate in the center and is formed prismatically outside the plate.

6. The prismatic element according to claim 1, wherein a plane-parallel plate has an elongated shape and there is a wedge-shaped reduction in the prismatic arrangement in longitudinal direction of the plate.

* * * * *